(12) United States Patent
Hoernig

(10) Patent No.: US 9,888,893 B2
(45) Date of Patent: Feb. 13, 2018

(54) METHOD AND APPARATUS FOR COMBINED DUAL-ENERGY MAMMOGRAPHY AND TOMOSYNTHESIS IMAGING

(71) Applicant: Siemens Aktiengesellschaft, Munich (DE)

(72) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 139 days.

(21) Appl. No.: 14/796,319

(22) Filed: Jul. 10, 2015

(65) Prior Publication Data

US 2016/0007943 A1 Jan. 14, 2016

(30) Foreign Application Priority Data

Jul. 10, 2014 (DE) .................. 10 2014 213 464

(51) Int. Cl.
*A61B 6/04* (2006.01)
*A61B 6/00* (2006.01)
(Continued)

(52) U.S. Cl.
CPC .............. *A61B 6/482* (2013.01); *A61B 6/025* (2013.01); *A61B 6/481* (2013.01); *A61B 6/502* (2013.01); *A61B 6/545* (2013.01); *G06T 5/50* (2013.01); *A61B 6/5235* (2013.01); *A61B 6/548* (2013.01); *G06T 2207/10116* (2013.01); *G06T 2207/20224* (2013.01); *G06T 2207/30101* (2013.01)

(58) Field of Classification Search
CPC ......... A61B 6/025; A61B 6/481; A61B 6/482; A61B 6/502; A61B 6/5235; A61B 6/545; A61B 6/548; A61B 6/032; A61B 6/4085; A61B 6/027; A61B 6/4291; A61B 6/4028; A61B 6/5282; A61B 6/06; A61B 6/583; A61B 6/4035; A61B 6/466; A61B 6/4441; A61B 6/4488; A61B 6/463; A61B 6/0414; A61B 6/0435; G06F 13/362; G06F 13/4295; G06F 1/3253; G06T 2207/10116; G06T 2207/20224; G06T 2207/30101; G06T 5/50
USPC ..... 378/4, 8, 22, 98.8, 37, 62; 382/128, 130, 382/131; 600/431
See application file for complete search history.

(56) References Cited

U.S. PATENT DOCUMENTS 6,618,466 B1 9/2003 Ning
8,594,274 B2 11/2013 Hoernig et al.
(Continued)

*Primary Examiner* — Irakli Kiknadze
(74) *Attorney, Agent, or Firm* — Schiff Hardin LLP

(57) ABSTRACT

In a method and tomosynthesis apparatus for combined dual-energy mammography and tomosynthesis imaging of a predetermined volume of an examination subject, while contrast agent is flowing through the volume, an x-ray source is set to radiate x-rays at low and high radiation energy. A pre-shot of the volume is obtained with the high radiation energy, and recording parameters for high-energy images, low-energy images, and low-energy tomosynthesis scans are obtained from the pre-shot. A high-energy image is then obtained, followed by operating the x-ray source at a low energy, and a low-energy tomosynthesis scan of the volume is executed using the recording parameters, and a two-dimensional low-energy image of the volume is generated during the low-energy tomosynthesis scan.

14 Claims, 3 Drawing Sheets

(51) Int. Cl.
*A61B 6/02* (2006.01)
*G06T 5/50* (2006.01)

(56) References Cited

U.S. PATENT DOCUMENTS

| | | | |
|---|---|---|---|
| 2002/0085672 A1 | 7/2002 | Ganin et al. | |
| 2004/0264626 A1* | 12/2004 | Besson | A61B 6/032 378/4 |
| 2012/0134464 A1* | 5/2012 | Hoernig | A61B 6/025 378/22 |
| 2012/0238870 A1* | 9/2012 | Smith | A61B 6/025 600/431 |

* cited by examiner

METHOD AND APPARATUS FOR COMBINED DUAL-ENERGY MAMMOGRAPHY AND TOMOSYNTHESIS IMAGING

BACKGROUND OF THE INVENTION

Field of the Invention

The invention concerns a method and apparatus for combined dual-energy mammography and tomosynthesis imaging of a predetermined volume of an object under examination while a contrast agent is flowing through the volume.

Description of the Prior Art

In x-ray mammography, tomosynthesis scans of the breast and their three-dimensional reconstructions as tomograms are state of the art as a diagnostic method, while two-dimensional mammography images (mammograms) are used primarily for monitoring (screening) procedures and as images for comparison with images previously recorded. Digital tomosynthesis is understood as meaning a combination of digital image capture and image processing, with minimal movement of the x-ray source. Tomosynthesis has similarities to computed tomography (CT), but is regarded as a separate modality. While in the case of computed tomography, projection images are created during a full 360° rotation of the x-ray source around the object under examination, in the case of tomosynthesis the x-ray source rotates only through a small angle, for example 40°, with only a small number of projection images being created (typically between 7 and 60). The use of highly resolving detectors allows a very high resolution in planes perpendicular to the axis referred to as the Z axis (the axis in the direction of the 0° tomosynthesis angle or the perpendicular direction from the x-ray source to the detector or CC alignment (cranial-caudal=from head to foot)), even if the resolution in the direction of the Z axis is less. In comparison with mammography, tomosynthesis operates with a lower radiation dose per projection.

Also known is the mode referred to as the combined 2D/3D mode, in which two-dimensional mammographic images are also recorded within a tomosynthesis scan. The typical procedure here is that, with an inserted anti-diffusion grid in the central (0° CC) direction of projection (for CC=cranial caudal and MLO=medio lateral oblique), after the recording of the pre-shot, which is used for calculating the mAs required for the projections, a main shot of x-radiation is triggered, creating the mammographic image. Subsequently, the anti-diffusion grid is withdrawn and the tomosynthesis scan is started. By this combined mode, both a two-dimensional mammographic image (mammogram) and a 3D tomogram of the breast in the same position and under identical compression are created.

Contrast-enhanced dual-energy mammography (CE-DEM) is a relatively new diagnostic method. In this method, with a contrast agent flowing through the patient, two-dimensional low-energy images and two-dimensional high-energy images are respectively recorded and subsequently subtracted from one another, in order to make the concentration of the contrast agent visible. The application of CEDEM to 3D imaging is also known (contrast-enhanced dual-energy tomosynthesis, CEDET). Virtual 2D mammographic images calculated from a tomosynthesis scan are also known, but are not regarded as fully equivalent to a recorded 2D mammographic image. DE 10 2010 041 920 A1 discloses a method in which first a low-energy image, then a high-energy image and a high-energy tomosynthesis scan are created and the low-energy image is subtracted from the high-energy images.

Images recorded without a grid (that is to say an image recorded without an anti-diffusion grid for filtering out undesired diffused radiation) for contrast-enhanced mammography are known. In these cases, the diffused radiation correction is performed by software (for example Siemens Inspiration PRIME=Progressive Reconstruction Intelligently Minimizing Exposure). A disadvantage of this solution is that it is not associated with a tomosynthesis scan (from different directions of projection) and always leads to different breast positioning, which makes a diagnosis more difficult (for example due to poor positioning, nipple retraction, cutting off of the tissue near the breast wall, etc.) or alternatively leads to much longer breast compression for the patient.

SUMMARY OF THE INVENTION

An object of the present invention is to provide a method that overcomes the disadvantages of known systems as described above, as well as an x-ray apparatus that is suitable for implementing the method.

In the method according to the invention for combined dual-energy mammography and tomosynthesis imaging of a predetermined volume of an object under examination while a contrast agent is flowing through the volume by operation of a tomosynthesis apparatus, a high energy supply to an x-ray source of the tomosynthesis apparatus is set for a high radiation energy. A pre-shot of the predetermined volume with the high radiation energy is obtained. Recording (data acquisition) parameters of the tomosynthesis apparatus for high-energy images, for low-energy images and for low-energy tomosynthesis scans are calculated from the pre-shot by an AEC (Automatic Exposure Control) device. A two-dimensional high-energy image of the predetermined volume with the high radiation energy is produced by using the recording parameters calculated for high-energy images. After the high-energy image is produced, a low energy supply to the x-ray source of the tomosynthesis apparatus is set for a low radiation energy, the high radiation energy being much higher than the low radiation energy. A two-dimensional low-energy image of the predetermined volume is generated with the low radiation energy by using the recording parameters calculated for low-energy images. A low-energy tomosynthesis scan of the predetermined volume is generated by using the recording parameters calculated for the low-energy tomosynthesis scan, with the low-energy image being created during the low-energy tomosynthesis scan.

In the method according to the invention, it is possible very easily and in a very short time to be able to create both a contrast-enhanced mammogram and a 3D tomogram of the breast with an identical position and compression of the breast from a combined scan, it being possible for the x-ray dose acting on the breast to be reduced significantly, for example typically by up to 30%. In addition, it is also possible by the method according to the invention to create a synthetic mammogram additionally as a third view in addition to the tomosynthesis scan and the recombined contrast-enhanced mammogram. The optimum sequence of the scans does away with waiting times that occur in the case of known methods for the switching over of the x-ray window, since the switching operation can be performed easily during the approach to the outer scanning angle. The calculation of the recording parameters can likewise be carried out quickly and easily from the high-energy pre-shot. The method according to the invention allows an examination that is comprehensive and at the same time safe and unstressful for the patient.

For optimum image processing and presentation of the examination results, the following steps are additionally implemented. The two-dimensional low-energy image is subtracted from the two-dimensional high-energy image, in order to produce a resulting image in which the concentration of the contrast agent is visible, and the image data of the low-energy tomosynthesis scan are reconstructed into a three-dimensional volume image.

In this way, at least one optimum contrast-enhanced dual-energy mammogram is created.

In an embodiment of the invention, all of the images are recorded without the use of an anti-diffusion grid in the beam. For this purpose, if, for example, a movable anti-diffusion grid is present, before carrying out the method the grid is moved out of the beam and left there. Without the anti-diffusion grid, there are no artefacts due to grid movements (known as grid lines) in the contrast-enhanced mammogram, which brings about improved imaging. In the case of known methods, it is usual to move the anti-diffusion grid in and out again. In comparison with this, time can be saved in the case of the method of the invention, since the grid movements, such as withdrawing it, do not occur.

In an embodiment for high-quality x-ray imaging, a first x-ray filter setting is used during the recording of the high-energy image and a second x-ray filter setting, different from the first x-ray filter setting, is used during the recording of the low-energy image and the low-energy tomosynthesis scan. Switching over between the filter settings is performed after recording the two-dimensional high-energy image. As filters, Ti, Rh or Cu filters may be used for example, it being possible for these to differ, for example in thickness, in the high-energy imaging and in the low-energy imaging.

According to a further embodiment of the invention, the positioning of the object under examination does not change during the method. Due to the sequence of the method, good examination results can thus be produced, and at the same time the examination can be made as comfortable as possible for the patient, since there is no longer any need for unpleasant and laborious repositioning adjustments.

According to a further embodiment of the invention, the two-dimensional low-energy image is formed from a projection image of the low-energy tomosynthesis scan with a central direction of projection, in particular with a 0° cranial-caudal alignment, of the x-ray source. Use of the central projection allows an optimum image to be produced later when creating the contrast-enhanced dual-energy mammogram.

In an embodiment for keeping the x-ray dose to a level that protects the patient, a higher x-ray dose is set during the recording of the two-dimensional low-energy image than during the recording of the low-energy tomosynthesis scan. The switching can be carried out easily and without any loss of time.

According to an embodiment of the invention, a diffused radiation correction of the recorded pre-shots, high-energy images, low-energy images and/or low-energy tomosynthesis scans is implemented by a software algorithm. Since the images have been recorded without an anti-diffusion grid, such a correction is advantageous and can be performed easily by known software.

According to a further embodiment of the invention, recording parameters of the tomosynthesis machine are calculated from the pre-shot by means of the AEC device for at least one further high-energy image, at least one further low-energy image and at least one further low-energy tomosynthesis scan, and subsequently used for creating the corresponding images. In this way, a multiplicity of recording parameters for a multiplicity of further images can be calculated easily from a pre-shot created on one occasion. The recording parameters can be subsequently used, for example in creating a two-dimensional high-energy image of the predetermined volume with the high radiation energy by using the recording parameters calculated for high-energy images, setting a low energy supply, creating a two-dimensional low-energy image with the low radiation energy by using the recording parameters calculated for low-energy images, and creating a low-energy tomosynthesis scan, the low-energy image being created during the low-energy tomosynthesis scan. If required, any number of recording parameters can be determined from the pre-shot.

For implementing the method according to the invention, a tomosynthesis apparatus with a detector and an x-ray source for the emission of x-rays directed at the detector is used, an object under examination being positionable between the x-ray source and the detector such that the x-rays pass through a predetermined volume of the object under examination before they strike the detector. The tomosynthesis apparatus has a controller for activating the x-ray source and the detector and an image calculating unit for receiving data of the predetermined volume captured by the detector and for creating 2D high-energy and low-energy images and 3D low-energy tomosynthesis scans. The x-ray source is set by the controller in a switchable manner with a high energy supply for a high radiation energy and with a low energy supply for a low radiation energy, and the tomosynthesis machine having an AEC device for calculating recording parameters for high-energy images, for low-energy images and for low-energy tomosynthesis scans from a pre-shot.

For quick and easy evaluation of the measuring results, the image calculating unit is designed for producing a result that represents a concentration of a contrast agent in the predetermined volume portion.

The tomosynthesis apparatus can also have an x-ray filter device with at least two x-ray filter settings, in particular a first x-ray filter setting being optimized for a high-energy image and a second x-ray filter setting being optimized for a low-energy image.

The tomosynthesis apparatus can have an anti-diffusion grid, which can be brought into the beam of the x-rays, and can be removed from the beam.

DESCRIPTION OF THE PREFERRED EMBODIMENTS

Figure 1:
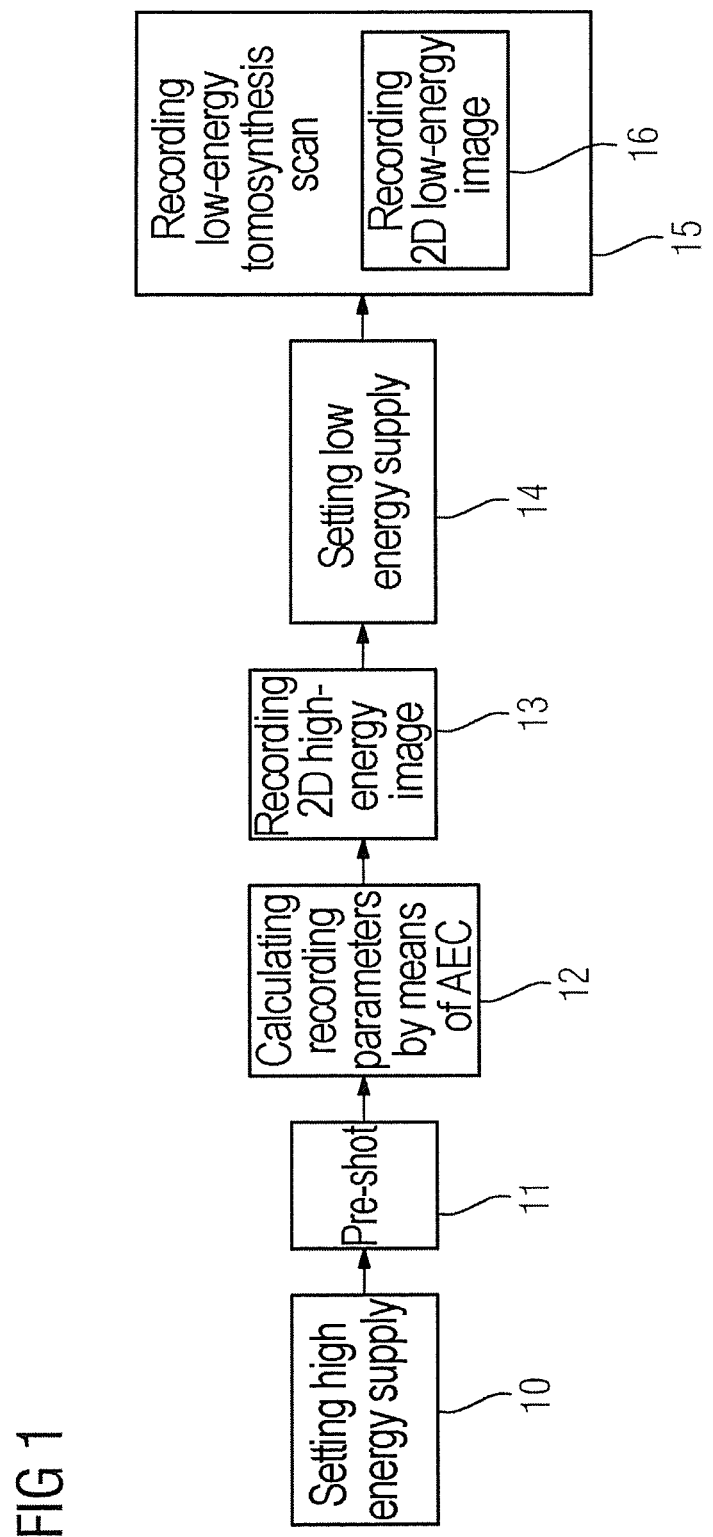
FIG. 1 shows a sequence of the method according to the invention.

FIG. 1 shows the sequence of the method according to the invention for combined dual-energy mammography and tomosynthesis imaging, by which both a contrast-enhanced mammogram and a 3D tomogram of the breast with an identical position and compression of the breast can be created easily and in a very short time from a combined scan, the duration of compression of the breast being minimized and the x-ray dose acting on the breast being significantly reduced.

Before the beginning of the method, a breast of a male or female patient is positioned, for example by the breast being arranged on the x-ray detector by means of a compression plate. For improved image quality, a contrast agent may also be administered to the patient (injected) immediately before beginning the method. The entire method is preferably carried out without the use of an anti-diffusion grid. If the tomosynthesis machine used for the method has an anti-diffusion grid, it is moved out of the beam before carrying out the method.

In a first step 10, a high energy supply, i.e. high x-ray radiation energy, is set for recording high-energy images. Such a high x-ray radiation energy may for example lie in the range from 40 to 50 kVp, while for example typical low x-ray radiation energies may lie in the range from 20 to 35 kVp. Generally, this is controlled by way of the tube voltage. Together with the setting of the high energy supply, a suitable high-energy x-ray filter may also be selected and set. Such a high-energy x-ray filter may for example be formed from titanium or copper, or at least partially contain these materials.

Subsequently, in a second step 11, what is known as a pre-shot, that is to say a preliminary image, of the predetermined region of the patient's breast is recorded. Such a pre-shot is generally recorded with a very small recording time, in order to keep the x-ray dose low and not to expose the patient to too much radiation. Just like the individual 2D images generally, such a pre-shot is recorded in a central direction of projection, in particular for example with a 0° cranio-caudal (CC) or medio lateral oblique (MLO) alignment, of the x-ray source.

In a third step 12, all the necessary recording parameters for the other images are determined from the pre-shot read out from the x-ray detector, in that they are determined or calculated by means of a device known as an AEC device (Automatic Exposure Control). This involves calculating at least the tube current/time product (mAs) that is respectively suitable for the 2D high-energy image, for the 2D low-energy image and for the low-energy tomosynthesis scan. AEC devices are known from the prior art and are implemented in the case of most known x-ray machines.

In a fourth step 13, subsequently a 2D high-energy image is recorded by using the corresponding tube current/time product (mAs) determined by the AEC device and read out from the x-ray detector. Subsequently, in a fifth step 14, a low energy supply, that is to say a low x-ray radiation energy, is set for recording low-energy images. Generally, this is in turn controlled by way of the tube voltage. In addition, the x-ray filter or filters may also be changed and a filter that is suitable for low-energy images selected and set (for example a filter with a smaller thickness than in the case of the high-energy imaging).

Subsequently, in a sixth step 15, a low-energy tomosynthesis scan is recorded by using recording parameters calculated by means of the AEC device and read out from the x-ray detector. For this, a number (about between 7 and 60) of projection images of the predetermined volume of the patient's breast are recorded from different projection angles. The seventh step 16, in which a 2D low-energy image is recorded, is integrated into the sixth step 15. This is realized by for example the central projection (0° alignment CC) of the low-energy tomosynthesis scan being formed from the 2D low-energy image. The recording of the 2D low-energy image may differ for example from the other projection images of the low-energy tomosynthesis scan by a higher x-ray dose, that is to say that, with the tube voltage remaining the same, the tube current or the recording time may be higher in the case of the 2D low-energy image.

All of the recordings of the method are carried out without the use of an anti-diffusion grid. In order nevertheless to be able to carry out a diffused radiation correction of the recordings and images read out from the x-ray detector, known software algorithms may be used for example. An example of such software is the Siemens Inspiration PRIME (Progressive Reconstruction Intelligently Minimizing Exposure) from the company Siemens AG.

For better utilization of a previously injected contrast agent, the steps of the method are carried out as quickly as possible one after the other. This is easily possible with automatic activation of the method, for example by a control unit.

Figure 2:
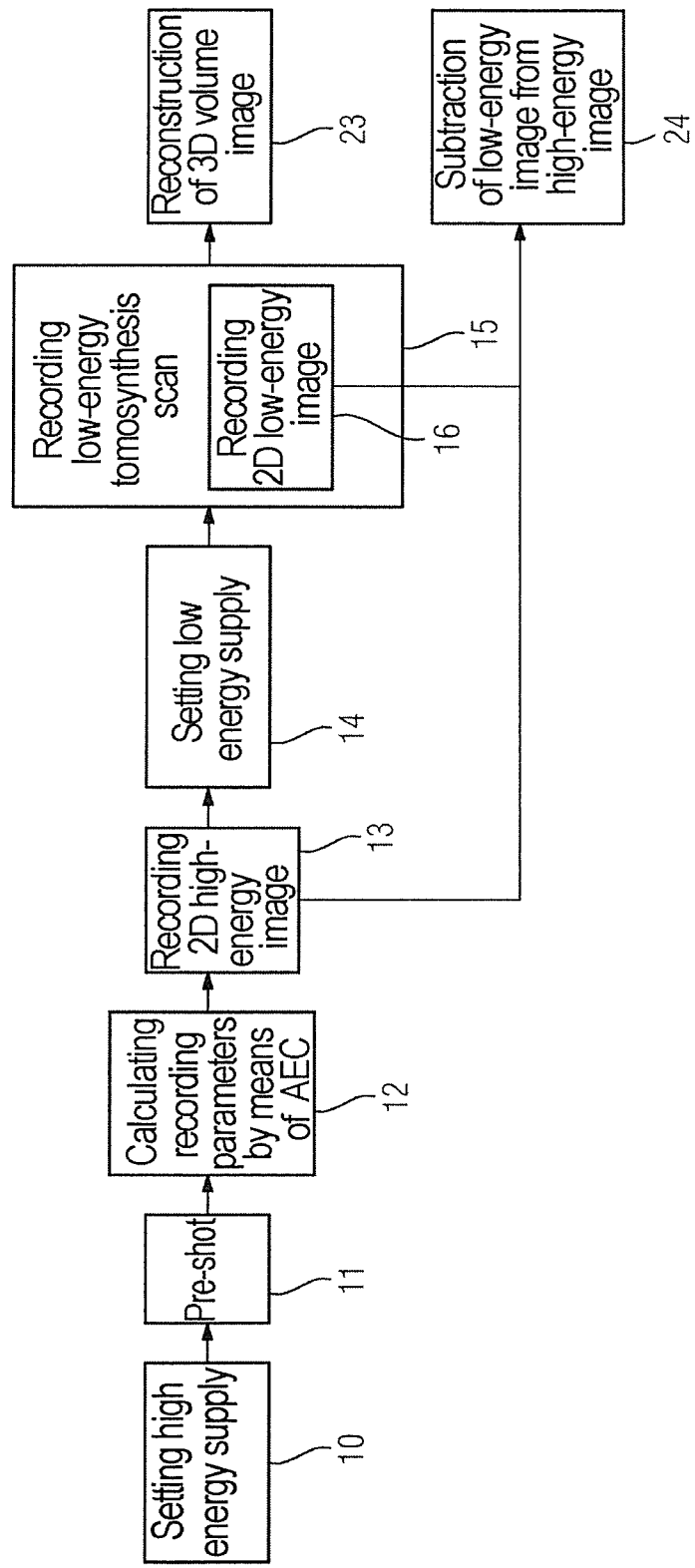
FIG. 2 shows an extended sequence of the method according to the invention.

In FIG. 2, an extension of the method shown in FIG. 1 with two further steps is described. Thus, in an eighth step 23, the read-out projection recordings of the low-energy tomosynthesis scan are reconstructed into a 3D volume image of the predetermined volume, for example by means of an image calculating unit. This is generally carried out by means of known reconstruction algorithms. Furthermore, in a ninth step 24 (which may also be carried out before the eighth step or at the same time as it), a weighted subtraction of the 2D low-energy image from the 2D high-energy image is carried out, whereby an image known as a recombined contrast-enhanced mammogram is created. By means of such a recombined contrast-enhanced mammogram, a particularly precise and high-quality representation of a concentration of a contrast agent in the predetermined volume portion is possible. The 2D low-energy image and the 2D high-energy image should generally have been recorded in the same direction of projection of the x-ray source in order to be able to carry out a meaningful combination.

Figure 3:
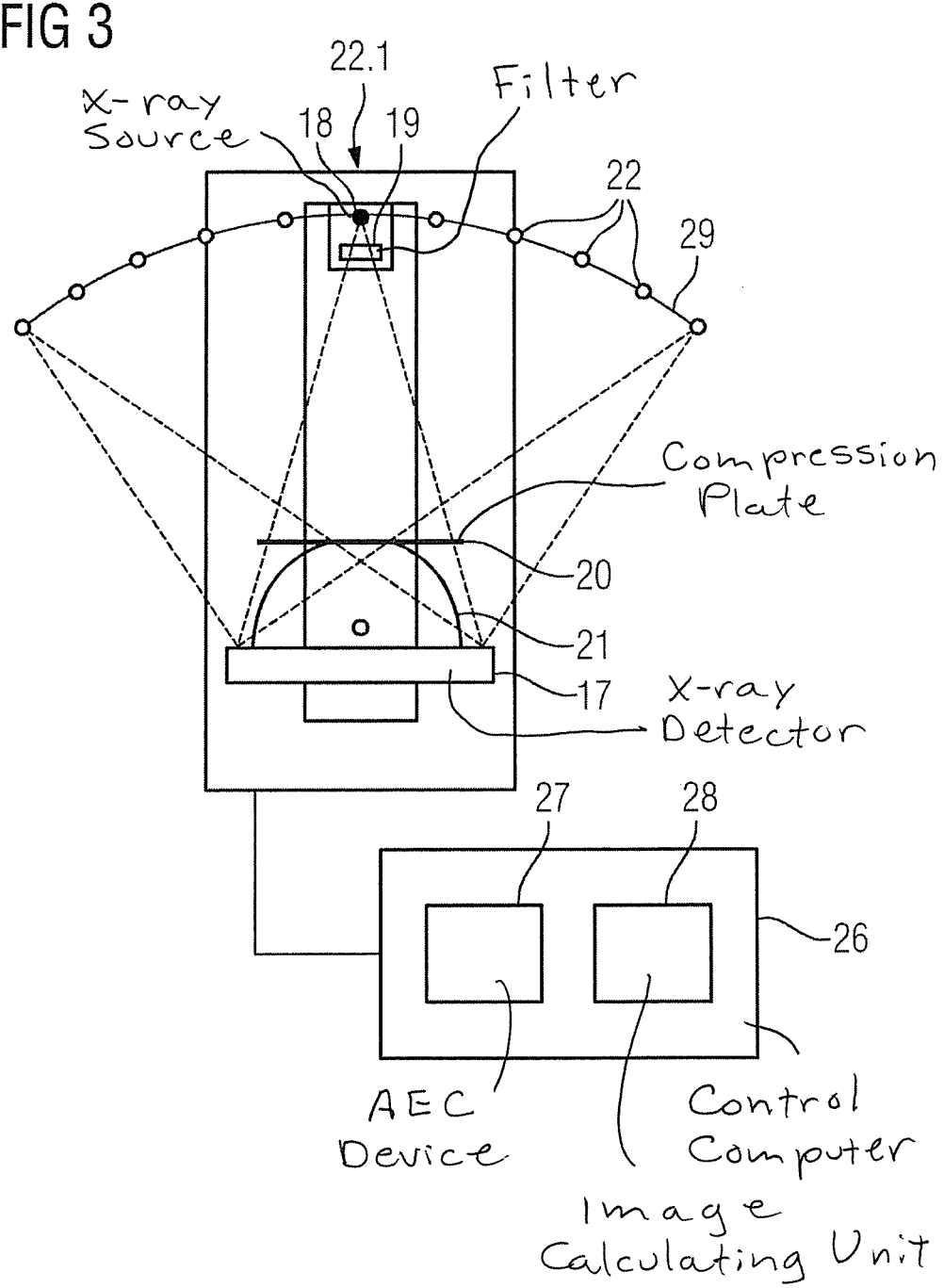
FIG. 3 shows a view of a typical mammography-tomosynthesis machine with an indicated swiveling path of the x-ray source.

FIG. 3 shows a tomosynthesis machine designed for mammographic imaging that is suitable for carrying out the method according to the invention. Such a tomosynthesis machine has an x-ray source 18 for emitting an x-radiation and also an x-ray detector 17 for detecting the x-radiation. An object under examination in the form of a breast 21 is arranged between the x-ray source 18 and the x-ray detector 17 by a compression plate 20, so that the x-radiation passes through a predetermined volume of the object under examination and subsequently impinges on the x-ray detector 17. The x-ray source 18 is also arranged in such a way that it can swivel, so that, in addition to the central recording position 22.1, it can also assume further recording positions in different directions of projection with respect to the object under examination. The swiveling capability is indicated in FIG. 3 by the arc of a circle 29. The typical number of recording positions lies between 7 and 60.

The x-ray source is also designed in such a way that it can emit at least two radiation energies of different levels, that is to say a high radiation energy and a low radiation energy. For this, generally tube voltages of different levels are set and the x-ray source is designed to be switchable between these tube voltages. Furthermore, an x-ray filter device 19 is arranged, and preferably it is possible to select between at least two different x-ray filters, which are then positioned with an appropriate setting in the beam.

The tomosynthesis apparatus also has a control computer, 26 for activating the x-ray source and the x-ray detector and also for activating the method according to the invention. Furthermore, the tomosynthesis machine has an image calculating unit 28, which is designed for receiving the image data of the predetermined volume of the object under examination received by the x-ray detector and read out from the x-ray detector and for creating 2D high-energy and low-energy images and 3D low-energy tomosynthesis scans. Furthermore, the tomosynthesis machine has an AEC device 27 (Automatic Exposure Control), which is designed for calculating recording parameters for high-energy images, for low-energy images and for low-energy tomosynthesis scans from x-ray images, in particular also from a pre-shot. Such AEC devices are known. The tomosynthesis apparatus also has an anti-scattering grid (not shown), which is arranged such that it can be moved into the beam and can be removed from it.

The advantages of the method according to the invention, in which a high-energy image and also a low-energy image are created without a grid within a tomosynthesis scan, with the positioning of the breast remaining the same, are that both a contrast-enhanced mammogram and a 3D tomogram of the breast with an identical position and compression of the breast can be created, it being possible to reduce the glandular dose significantly (typically by up to about 30%); furthermore, there are no longer any artefacts due to grid movements (known as grid lines) in the contrast-enhanced mammogram, the creation of a synthetic mammogram (simulated mammogram from tomosynthesis scan) additionally as a third view, along with the tomosynthesis scan and the recombined contrast-enhanced mammography, becomes possible, the waiting times for the grid movements, such as the withdrawal, no longer occur and the times for the switching over of the x-ray window, as arise in the case of previously known methods, no longer occur, since the change can preferably take place during the approach to the outer scanning angle.

The invention can be briefly summarized as follows. For an examination of the breast that is particularly safe and comfortable for a patient, a method for the combined dual-energy mammography and tomosynthesis imaging of a predetermined volume of an object under examination while a contrast agent is flowing through by means of a tomosynthesis machine is provided, the method includes the following steps.

A high energy supply to an x-ray source of the tomosynthesis apparatus is set for a high radiation energy. A pre-shot of the predetermined volume with the high radiation energy is obtained. Recording (data acquisition) parameters of the tomosynthesis apparatus for high-energy images, for low-energy images and for low-energy tomosynthesis scans are calculated from the pre-shot by an AEC (Automatic Exposure Control) device. A two-dimensional high-energy image of the predetermined volume with the high radiation energy is produced by using the recording parameters calculated for high-energy images. After the high-energy image is produced, a low energy supply to the x-ray source of the tomosynthesis apparatus is set for a low radiation energy, the high radiation energy being much higher than the low radiation energy. A two-dimensional low-energy image of the predetermined volume is generated with the low radiation energy by using the recording parameters calculated for low-energy images. A low-energy tomosynthesis scan of the predetermined volume is generated by using the recording parameters calculated for the low-energy tomosynthesis scan, with the low-energy image being created during the low-energy tomosynthesis scan.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for combined dual-energy mammography and tomosynthesis imaging of a predetermined volume of an object under examination, while a contrast agent is flowing through the volume, by operation of a tomosynthesis apparatus having an x-ray source supplied by an energy supply, said method comprising:

setting pre-shot imaging parameters for said tomosynthesis apparatus that include setting said energy supply for a high radiation energy;

operating the tomosynthesis apparatus with said pre-shot recording parameters, and with said x-ray source at a single position relative to the predetermined volume, in order to obtain a pre-shot of the predetermined volume with the high radiation energy;

providing the pre-shot to a processor and, in said processor, calculating recording parameters, from said pre-shot, of the tomosynthesis apparatus for high-energy diagnostic images, for low-energy diagnostic images, and for low-energy tomosynthesis scans by operation of an AEC (Automatic Exposure Control) device, with the recording parameters for the high-energy diagnostic images differing from said pre-shot recording parameters but both including said energy supply set at said high radiation energy, and with the recording parameters for the low-energy diagnostic images differing from the recording parameters for the low-energy tomosynthesis scans, but including a same low radiation energy setting of said energy supply;

operating the tomosynthesis apparatus, with the x-ray source at said single position relative to the predetermined volume, using the recording parameters calculated for low-energy diagnostic images, in order to produce a two-dimensional high-energy diagnostic image of the predetermined volume;

after producing the two-dimensional high-energy diagnostic image, setting said energy supply to said low radiation energy, said low radiation energy being much lower than said high radiation energy;

operating said tomosynthesis apparatus with said recording parameters for said low energy tomosynthesis scans by moving said x-ray source through a plurality of different positions relative to said predetermined volume of said object in order to obtain a plurality of projection images, each with said energy supply at said low radiation energy setting of the predetermined volume, said plurality of positions including said single position; and during said low-energy tomosynthesis scan, when said x-ray source is at said single position, operating said tomosynthesis apparatus with said recording parameters for said low-energy diagnostic images, in order to produce a low-energy diagnostic image of the predetermined volume with said energy supply at said low radiation energy setting.

2. The method as claimed in claim 1, comprising:

subtracting the two-dimensional low-energy diagnostic image from the two-dimensional high-energy diagnostic image, in order to create a result with which the concentration of the contrast agent is visible; and reconstructing the projection images of the low-energy tomosynthesis scan into a three-dimensional volume image.

3. The method as claimed in claim 1, comprising recording all of the images without an anti-diffusion grid in the beam.

4. The method as claimed in claim 1, comprising using a first x-ray filter setting during the recording of the high-energy diagnostic image and using a second x-ray filter setting, different from the first x-ray filter setting, during the recording of the low-energy diagnostic image and the low-energy tomosynthesis scan.

5. The method as claimed in claim 1, comprising maintaining an unchanging position of the object under examination during the method.

6. The method as claimed in claim 1, comprising setting a higher x-ray dose during the recording of the two-dimensional low-energy diagnostic image than during the recording of the low-energy tomosynthesis scan.

7. The method as claimed in claim 1, comprising executing at least one of a diffused radiation correction of the recorded pre-shot, high-energy diagnostic image, low-energy diagnostic image and low-energy tomosynthesis scans with a software algorithm.

8. The method as claimed in claim 1, comprising calculating recording parameters of the tomosynthesis apparatus from the pre-shot by the AEC device for at least one further high-energy image, at least one further low-energy image and at least one further low-energy tomosynthesis scan, that is subsequently used for creating the corresponding images.

9. A method as claimed in claim 1 comprising selecting said single position of said x-ray source as a central projection direction of said low-energy tomosynthesis scan.

10. The method as claimed in claim 9, wherein said central projection direction is a 0° cranial-caudal alignment of the x-ray source relative to the object.

11. A tomosynthesis apparatus for combined dual-energy mammography and tomosynthesis imaging of a predetermined volume of an object under examination, while a contrast agent is flowing through the volume, said tomosynthesis apparatus comprising:

an x-ray source that is movable through a number of different positions relative to said predetermined volume;

an energy supply for said x-ray source;

an x-ray detector that detects x-rays emitted by said x-ray source after attenuation of said x-rays by said predetermined volume;

a processor configured to set pre-shot imaging parameters for said x-ray source that include setting said energy supply for a high radiation energy;

said processor being configured to operate the x-ray source with said pre-shot recording parameters, and with said x-ray source at a single position relative to the predetermined volume, in order to obtain a pre-shot of the predetermined volume with the high radiation energy;

said processor being provided with the pre-shot and said processor being configured to calculate recording parameters, from said pre-shot, of the x-ray source for high-energy diagnostic images, for low-energy diagnostic images, and for low-energy tomosynthesis scans by operation of an AEC (Automatic Exposure Control) device, with the recording parameters for the high-energy diagnostic images differing from said pre-shot recording parameters but both including said energy supply set at said high radiation energy, and with the recording parameters for the low-energy diagnostic images differing from the recording parameters for the low-energy tomosynthesis scans, but including a same low radiation energy setting of said energy supply;

said processor being configured to operate the x-ray source, with the x-ray source at said single position relative to the predetermined volume, using the recording parameters calculated for low-energy diagnostic images, in order to produce a two-dimensional high-energy diagnostic image of the predetermined volume;

said processor being configured to set said energy supply to said low radiation energy, after producing the two-dimensional high-energy diagnostic image, said low radiation energy being much lower than said high radiation energy;

said processor being configured to operate said x-ray source with said recording parameters for said low energy tomosynthesis scans by moving said x-ray source through a plurality of different positions relative to said predetermined volume of said object in order to obtain a plurality of projection images, each with said energy supply at said low radiation energy setting of the predetermined volume, said plurality of positions including said single position; and during said low-energy tomosynthesis scan, when said x-ray source is at said single position, said processor being configured to operate said tomosynthesis apparatus with said recording parameters for said low-energy diagnostic images, in order to produce a low-energy diagnostic image of the predetermined volume with said energy supply at said low radiation energy setting.

12. The tomosynthesis apparatus as claimed in claim 11, wherein the image calculating computer is configured to produce a result that represents a concentration of a contrast agent in the predetermined volume portion.

13. The tomosynthesis apparatus as claimed in claim 11, comprising an x-ray filter device with at least two x-ray filter settings disposed in said beam.

14. The tomosynthesis apparatus, as claimed in claim 11 comprising an anti-diffusion grid that is moveable into and out of the beam.

* * * * *